US007659055B2

(12) United States Patent
Magdalena et al.

(10) Patent No.: US 7,659,055 B2
(45) Date of Patent: Feb. 9, 2010

(54) **FRAGMENTS OF NUCLEIC ACIDS SPECIFIC TO MYCOBACTERIA WHICH ARE MEMBERS OF THE *M. TUBERCULOSIS* COMPLEX AND THEIR APPLICATIONS FOR THE DETECTION AND THE DIFFERENTIAL DIAGNOSIS OF MEMBERS OF THE *M. TUBERCULOSIS* COMPLEX**

(75) Inventors: Juana Magdalena, Brussels (BE); Philip Supply, Bourghelles (FR); Camille Locht, Brussels (BE)

(73) Assignees: Institut Pasteur de Lille, Lille (FR); Institut National de la Sante et de la Recherche Medicale, Paris (FR)

(*) Notice: Subject to any disclaimer, the term of this patent is extended or adjusted under 35 U.S.C. 154(b) by 87 days.

(21) Appl. No.: 10/086,206

(22) Filed: Feb. 28, 2002

(65) Prior Publication Data

US 2003/0124546 A1 Jul. 3, 2003

Related U.S. Application Data

(63) Continuation of application No. 09/242,588, filed as application No. PCT/FR97/01483 on Aug. 12, 1997, now abandoned.

(30) Foreign Application Priority Data

Aug. 19, 1996 (FR) .................................. 96 10277

(51) Int. Cl.
*C12Q 1/68* (2006.01)
*C07H 21/04* (2006.01)
*C12P 19/34* (2006.01)
*C12N 15/00* (2006.01)

(52) U.S. Cl. ....................... 435/6; 435/91.2; 435/320.1; 435/810; 536/23.1; 536/24.32; 536/24.33

(58) Field of Classification Search ..................... 435/6, 435/91.2, 320.1, 810; 536/23.1, 23.7, 24.32, 536/24.33

See application file for complete search history.

(56) References Cited

U.S. PATENT DOCUMENTS 5,418,162 A * 5/1995 Blakely et al. .............. 435/348
5,474,796 A * 12/1995 Brennan .................... 427/2.13
5,700,683 A * 12/1997 Stover et al. ........... 435/252.31

OTHER PUBLICATIONS

Ahern, H. Biochemical, reagent kits offer scientists good return on investment. The Scientist 9(15):20 (Jul. 1995).*

* cited by examiner

*Primary Examiner*—Diana B Johannsen
(74) *Attorney, Agent, or Firm*—Lucas & Mercanti, LLP

(57) ABSTRACT

A fragment of a nucleic acid specific to mycobacteria of *M. tuberculosis* complex having a nucleotide sequence of SEQ ID No: 1 and SEQ ID No: 2 and their complimentary sequences.

20 Claims, 9 Drawing Sheets

GAATTCCGCTGCGCTACGACCTGGATTCCGCGATGAGGCCGCTGGTGCGCGGTGG 55
I P L R Y D L D S A M R P L V R G G
→ PgmY

TACGTATCTGGACCCGGAGGCGGCAGCCGCCGGCGCCGCCGCGGTGGCCGGCCAGGGCCG 115
T Y L D P E A A A A G A A A V A G Q G R

CGGGTAATTGTTTGAGATCCCACCTGCCGGCGGTTTCGGCGGCTGATGGTGTGCTTTGGT 175
G

GCGCTGTTTGCCAAACAGCATGTGAACGGTAACCGAACAGCTGTGGCGTAGTGTGTGACT 235

TGTCCGATTTTGGCCTTGCCGCGCTAGGGCGACGTTCACCGGATTTGTAGGATTTTCCTT 295
SD

GTGACTGTGTTCTCGGCGCTGTTGCTGGCCGGGGTTTTGTCCGCGCTGGCACTGGCCGTC 355
M T V F S A L L L A G V L S A L A L A V 20
SenX3 →

GGTGGTGCTGTTGGAATGCGGCTGACGTCGCGGGTCGTCGAACAGCGCCAACGGGTGGCC 415
G G A V G M R L T S R V V E Q R Q R V A 40

ACGGAGTGGTCGGGAATCACGGTTTCGCAGATGTTGCAATGCATTGTCACGCTGATGCCG 475
T E W S G I T V S Q M L Q C I V T L M P 60

CTGGGCGCCGCGGTGGTGGACACCCATCGCGACGTTGTCTACCTCAACGAACGGGCCAAA 535
L G A A V V D T H R D V V Y L N E R A K 80

GAGCTAGGTCTGGTGCGCGACCGCCAGCTCGATGATCAGGCCTGGCGGGCCGCCCGGCAG 595
E L G L V R D R Q L D D Q A W R A A R Q 100

GCGCTGGGTGGTGAAGACGTCGAGTCCGACCTGTCGCCGCGCAAGCGGTCGGCCACGGGT 655
A L G G E D V E S D L S P R K R S A T G 120

CGATCCGGGCTATCAGTGCATGGGCATGCCCGGTTGCTGAGCGAGGAAGACCGCCGGTTC 715
R S G L S V H G H A R L L S E E D R R F 140

GCCGTGGTGTTCGTGCACGACCAGTCGGATTATGCGCGGATGGAGGCGGCTAGGCGTGAC 775
A V V F V H D Q S D Y A R M E A A R R D 160

TTCGTGGCCAACGTCAGTCACGAGCTCAAGACGCCCGTCGGTGCCATGGCTCTACTCGCC 835
F V A N V S H E L K T P V G A M A L L A 180
↑ H

FIG.2

```
GAGGCGCTGCTGGCGTCGGCCGACGACTCCGAAACCGTTCGGCGGTTCGCCGAGAAGGTG    895
 E   A   L   L   A   S   A   D   D   S   E   T   V   R   R   F   A   E   K   V      200

CTCATTGAGGCCAACCGGCTCGGTGACATGGTCGCCGAGTTGATCGAGCTATCCCGGCTA    955
 L   I   E   A   N   R   L   G   D   M   V   A   E   L   I   E   L   S   R   L      220

CAGGGCGCCGAGCGGCTACCCAATATGACCGACGTCGACGTCGATACGATTGTGTCGGAA   1015
 Q   G   A   E   R   L   P   N   M   T   D   V   D   V   D   T   I   V   S   E      240

GCGATTTCACGCCATAAGGTGGCGGCCGACAACGCCGACATCGAAGTCCGCACCGACGCG   1075
 A   I   S   R   H   K   V   A   A   D   N   A   D   I   E   V   R   T   D   A      260

CCCAGCAATCTGCGGGTGCTGGGCGACCAAACTCTGCTGGTTACCGCACTGGCAAACCTG   1135
 P   S   N   L   R   V   L   G   D   Q   T   L   L   V   T   A   L   A   N   L      280
                                             ―――――――――――――――――
                                                             N

GTTTCCAATGCGATTGCCTATTCGCCGCGCGGGTCGCTGGTGTCGATCAGCCGTCGCCGT   1195
 V   S   N   A   I   A   Y   S   P   R   G   S   L   V   S   I   S   R   R   R      300
 ―――――――――――

CGCGGTGCCAACATCGAGATCGCCGTCACCGACCGGGGCATCGGCATCGCGCCGGAAGAC   1255
 R   G   A   N   I   E   I   A   V   T   D   R   G   I   G   I   A   P   E   D      320
                                 ―――――――――――――――――――――――――
                                             G1

CAGGAGCGGGTCTTCGAACGGTTCTTCCGGGGGGACAAGGCGCGCTCGCGTGCCACCGGA   1315
 Q   E   R   V   F   E   R   F   F   R   G   D   K   A   R   S   R   A   T   G      340
             ―――――――――――――
                 F

GGCAGCGGACTCGGGTTGGCCATCGTCAAACACGTCGCGGCTAATCACGACGGCACCATC   1375
 G   S   G   L   G   L   A   I   V   K   H   V   A   A   N   H   D   G   T   I      360
 ―――――――――――――――――
         G2

CGCGTGTGGAGCAAACCGGGAACCGGGTCAACGTTCACCTTGGCTCTTCCGGCGTTGATC   1435
 R   V   W   S   K   P   G   T   G   S   T   F   T   L   A   L   P   A   L   I      380

GAGGCCTATCACGACGACGAGCGACCCGAGCAGGCGCGAGAGCCCGAACTGCGGTCAAAC   1495
 E   A   Y   H   D   D   E   R   P   E   Q   A   R   E   P   E   L   R   S   N      400

AGGTCACAACGAGAGGAAGAGCTGAGCCGATGACCTGCGCCGACGACGATGCAGAGCGTA   1555
 R   S   Q   R   E   E   E   L   S   R      410
```

FIG. 2
(cont.)

```
GCGATGAGGTGGGGGCACCACCCGCTTGCGGGGGAGAGTGGCGCTGATGACCTGCGCCGA 1615

CGACGATGCAGAGCGTAGCGATGAGGTGGGGGCACCACCCGCTTGCGGGGGAGAGTGGCG 1675

CTGATGACCAGTGTGTTGATTGTGGAGGACGAGGAGTCGCTGGCCGATCCGCTGACGTTT 1735
    M   T   S   V   L   I   V   E   D   E   E   S   L   A   D   P   L   T   F    19
    RmgX3 →
CTGCTGCGCAAGGAGGGCTTTGAGGCCACGGTGGTGACCGATGGTCCGGCAGCTCTCGCC 1795
L   L   R   K   E   G   F   E   A   T   V   V   T   D   G   P   A   A   L   A    39

GAGTTCGACCGGGCCGGCGCCGACATCGTCCTGCTCGATCTGATGCTGCCTGGGATGTCG 1855
E   F   D   R   A   G   A   D   I   V   L   L   D   L   M   L   P   G   M   S    59

GGTACCGATGTATGCAAGCAGTTGCGCGCTCGGTCCAGCGTTCCGGTGATCATGGTGACC 1915
G   T   D   V   C   K   Q   L   R   A   R   S   S   V   P   V   I   M   V   T    79

GCCCGGGATAGCGAGATCGACAAGGTGGTCGGCCTGGAGCTGGGCGCTGACGACTACGTG 1975
A   R   D   S   E   I   D   K   V   V   G   L   E   L   G   A   D   D   Y   V    99

ACCAAGCCCTATTCGGCACGCGAGTTGATCGCACGCATCCGCGCGGTGCTGCGCCGTGGC 2035
T   K   P   Y   S   A   R   E   L   I   A   R   I   R   A   V   L   R   R   G   119

GGCGACGACGACTCGGAGATGAGCGATGGCGTGCTGGAGTCCGGGCCGGTTCGCATGGAT 2095
G   D   D   D   S   E   M   S   D   G   V   L   E   S   G   P   V   R   M   D   139

GTGGAGCGCCATGTCGTCTCGGTGAACGGTGACACCATCACGCTGCCGCTCAAGGAGTTC 2155
V   E   R   H   V   V   S   V   N   G   D   T   I   T   L   P   L   K   E   F   159

GACCTGCTGGAATACCTGATGCGCAACAGCGGGCGGGTGTTGACTCGCGGACAACTGATC 2215
D   L   L   E   Y   L   M   R   N   S   G   R   V   L   T   R   G   Q   L   I   179
```

GACCGGGTCTGGGGTGCGGACTACGTGGGCGACACCAAGACGCTCGACGTCCATGTCAAG 2275
D R V W G A D Y V G D T K T L D V H V K 199

CGGCTGCGCTCCAAGATCGAAGCCGACCCGGCTAACCCGGTTCACTTGGTGACGGTGCGC 2335
R L R S K I E A D P A N P V H L V T V R 219

GGGCTGGGCTACAAACTCGAGGGCTAGCGGACGCCGACAACCTTGGCGACTGTCTGGTCG 2395
G L G Y K L E G 227

GCTACGGCCAGTGCCATCGCCATGATGGACAGCTGCGGGTTCACTTCCGGGCAGCTGGGC 2455

AGGATCGAGGCGTCGGCAACCCACACGCCCTCGACGCCGCGCAGCCGGCCCGTCGCGTCG 2515

ACCGGACAAAGCTGCTCGTCGGCGCCGGCGGCCGCGGTGCCCGTCGGATGGAAGGCGGCC 2575

AGGTGCAGGCTTCTGGGGTTGGCTCGGCGCAGCACATCCTGCAGCTCGGGCAGGGACCGC 2635

ATCGGTGGGGCGCCGGGGATACCGGTCAGCACCTCCACCGCGCCGGCGGCAAAGAACAGC 2695

CGGCCAATGGCCTGCAGCGCGACCCGTAGCTTGGCGATCTCACCTGGAGCTATGTCATAG 2755

CGCACCACCGTCTCGCCGCGCACCGACCGCACCGTGCCGACGCCCCGATCGGCCACCATC 2815

GCCCCGAATGTTGCGATCTGCGGCGCCCGGTCGAGCCAGCGGAGCAGCTCGGCCCCGTAG 2875

CCGGGGAAGACCATCGACCCCATGCCCGGCGGTGTGGAGGTGGCCTCGATCAGCACGCCG 2935

TCGGATTCGTGAAACTCGTGAACCGCCGCGCTCTGCAGCACCCCGCGCCACGCGAAGACG 2995

TCGTCGTCGAAGAGCCCGGCCAGCATAGTTGCCGGGTGCAGCGCAAGGTTGTGGCCCAGT 3055

CGCGGTGCCCACCAAGACCGCTGCGCCGCAACAGCCCTGGCGTCTCCGTCGCACCGGCGG 3115

CGACGACGACCGCGTCGGCCAGCACGTCGAGTGTGGTGCCGTCGGGCCGGCGGGCTCGCA 3175

CGCCATAGGCCCGCCCGGCGCGGTGCAGGATCC 3208

A. BCG

GCT GAG CCG ATG ACC TGC GCC GAC GAC GAT GCA GAG CGT AGC GAT
M T C A D D D A E R S D
*senX3* → L S R *

GAG GTG GGG GCA CCA CCC GCT TGC GGG GGA GAG TGG CGC TGA TGA
E V G A P P A C G G E W R * *

M T

CCT GCG CCG ACG ACG ATG CAG AGC GTA GCG ATG AGG TGG GGG CAC

C A D D D A E R S D E V G A P

CAC CCG CTT GCG GGG GAG AGT GGC GCT GAT GAC CAG TGT

M T S V → *regX3*
P A C G G E W R * *

**B. *Mycobacterium tuberculosis***

GCT GAG CCG ATG ACC TGC GCC GAC GAC GAT GCA GAG CGT AGC GAT
M T C A D D D A E R S D
*senX3* → L S R *

GAG GTG GGG GCA CCA CCC GCT TGC GGG GGA GAG TGG CGC TGA TGA
E V G A P P A C G G E W R * *

M T

CCT GCG CCG ACG ACG ATG CAG AGC GTA GCG ATG AGG TGG GGG CAC

C A D D D A E R S D E V G A P

CAC CCG CTT GCG GGG GAG AGT GGC GCT GAT GAC CTG CGC CGA CGA

M T C A D D
P A C G G E W R * *

CGA TGC AGA GCG TAG CGA TGA GGA GGA GTG GCG CTG ATG ACC AGT
M T S → *regX3*
D A E R S D E E E W R * *

FIG. 4

SEQUENCE LISTING

```
<160> NUMBER OF SEQ ID NOS: 21

<210> SEQ ID NO 1
<211> LENGTH: 77
```

-continued

```
<212> TYPE: DNA
<213> ORGANISM: Mycobacterium tuberculosis

<400> SEQUENCE: 1

atgacctgcg ccgacgacga tgcagagcgt agcgatgagg tgggggcacc acccgcttgc     60

gggggagagt ggcgctg                                                    77


<210> SEQ ID NO 2
<211> LENGTH: 53
<212> TYPE: DNA
<213> ORGANISM: Mycobacterium tuberculosis

<400> SEQUENCE: 2

atgacctgcg ccgacgacga tgcagagcgt agcgatgagg aggagtggcg ctg            53


<210> SEQ ID NO 3
<211> LENGTH: 52
<212> TYPE: DNA
<213> ORGANISM: Mycobacterium leprae

<400> SEQUENCE: 3

atgacacccg cgcaggcgat gatgcagagc gaagtgacga gagggaatgt ga             52


<210> SEQ ID NO 4
<211> LENGTH: 19
<212> TYPE: DNA
<213> ORGANISM: Mycobacterium tuberculosis

<400> SEQUENCE: 4

gcgcgagagc ccgaactgc                                                  19


<210> SEQ ID NO 5
<211> LENGTH: 19
<212> TYPE: DNA
<213> ORGANISM: Mycobacterium tuberculosis

<400> SEQUENCE: 5

gcgcagcaga aacgtcagc                                                  19


<210> SEQ ID NO 6
<211> LENGTH: 23
<212> TYPE: DNA
<213> ORGANISM: Mycobacterium bovis

<400> SEQUENCE: 6

cgaggagtcg ctggccgatc cgc                                             23


<210> SEQ ID NO 7
<211> LENGTH: 22
<212> TYPE: DNA
<213> ORGANISM: Mycobacterium bovis

<400> SEQUENCE: 7

agcgccccag ctccagccga cc                                              22


<210> SEQ ID NO 8
<211> LENGTH: 21
<212> TYPE: DNA
<213> ORGANISM: Mycobacterium bovis

<400> SEQUENCE: 8

tggcgtagtg tgtgacttgt c                                               21
```

-continued

<210> SEQ ID NO 9
<211> LENGTH: 21
<212> TYPE: DNA
<213> ORGANISM: Mycobacterium bovis
<400> SEQUENCE: 9
gaccagacag tcgccaaggt t 21

<210> SEQ ID NO 10
<211> LENGTH: 20
<212> TYPE: DNA
<213> ORGANISM: Mycobacterium tuberculosis
<400> SEQUENCE: 10
aaacacgtcg cggctaatca 20

<210> SEQ ID NO 11
<211> LENGTH: 21
<212> TYPE: DNA
<213> ORGANISM: Mycobacterium tuberculosis
<400> SEQUENCE: 11
cctcaaagcc cctccttgcg c 21

<210> SEQ ID NO 12
<211> LENGTH: 3208
<212> TYPE: DNA
<213> ORGANISM: Mycobacterium bovis
<400> SEQUENCE: 12
gaattccgct gcgctacgac ctggattccg cgatgaggcc gctggtgcgc ggtggtacgt 60
atctggaccc ggaggcggca gccgccggcg ccgccgcggt ggccggccag ggccgcgggt 120
aattgtttga gatcccacct gccggcggtt tcggcggctg atggtgtgct ttggtgcgct 180
gtttgccaaa cagcatgtga acggtaaccg aacagctgtg gcgtagtgtg tgacttgtcc 240
gattttggcc ttgccgcgct agggcgacgt tcaccggatt tgtaggattt tccttgtgac 300
tgtgttctcg gcgctgttgc tggccggggt tttgtccgcg ctggcactgg ccgtcggtgg 360
tgctgttgga atgcggctga cgtcgcgggt cgtcgaacag cgccaacggg tggccacgga 420
gtggtcggga atcacggttt cgcagatgtt gcaatgcatt gtcacgctga tgccgctggg 480
cgccgcggtg gtggacaccc atcgcgacgt tgtctacctc aacgaacggg ccaaagagct 540
aggtctggtg cgcgaccgcc agctcgatga tcaggcctgg cgggccgccc ggcaggcgct 600
gggtggtgaa gacgtcgagt ccgacctgtc gccgcgcaag cggtcggcca cgggtcgatc 660
cgggctatca gtgcatgggc atgcccggtt gctgagcgag gaagaccgcc ggttcgccgt 720
ggtgttcgtg cacgaccagt cggattatgc gcggatggag gcggctaggc gtgacttcgt 780
ggccaacgtc agtcacgagc tcaagacgcc cgtcggtgcc atggctctac tcgccgaggc 840
gctgctggcg tcggccgacg actccgaaac cgttcggcgg ttcgccgaga aggtgctcat 900
tgaggccaac cggctcggtg acatggtcgc cgagttgatc gagctatccc ggctacaggg 960
cgccgagcgg ctacccaata tgaccgacgt cgacgtcgat acgattgtgt cggaagcgat 1020
ttcacgccat aaggtggcgg ccgacaacgc cgacatcgaa gtccgcaccg acgcgcccag 1080
caatctgcgg gtgctgggcg accaaactct gctggttacc gcactggcaa acctggtttc 1140
caatgcgatt gcctattcgc cgcgcgggtc gctggtgtcg atcagccgtc gccgtcgcgg 1200
tgccaacatc gagatcgccg tcaccgaccg gggcatcggc atcgcgccgg aagaccagga 1260

-continued

```
gcgggtcttc gaacggttct tccgggggga caaggcgcgc tcgcgtgcca ccggaggcag   1320

cggactcggg ttggccatcg tcaaacacgt cgcggctaat cacgacggca ccatccgcgt   1380

gtggagcaaa ccgggaaccg ggtcaacgtt caccttggct cttccggcgt tgatcgaggc   1440

ctatcacgac gacgagcgac ccgagcaggc gcgagagccc gaactgcggt caaacaggtc   1500

acaacgagag gaagagctga gccgatgacc tgcgccgacg acgatgcaga gcgtagcgat   1560

gaggtggggg caccacccgc ttgcggggga gagtggcgct gatgacctgc gccgacgacg   1620

atgcagagcg tagcgatgag gtgggggcac cacccgcttg cgggggagag tggcgctgat   1680

gaccagtgtg ttgattgtgg aggacgagga gtcgctggcc gatccgctga cgtttctgct   1740

gcgcaaggag ggctttgagg ccacggtggt gaccgatggt ccggcagctc tcgccgagtt   1800

cgaccgggcc ggcgccgaca tcgtcctgct cgatctgatg ctgcctggga tgtcgggtac   1860

cgatgtatgc aagcagttgc gcgctcggtc cagcgttccg gtgatcatgg tgaccgcccg   1920

ggatagcgag atcgacaagg tggtcggcct ggagctgggc gctgacgact acgtgaccaa   1980

gccctattcg gcacgcgagt tgatcgcacg catccgcgcg gtgctgcgcc gtggcggcga   2040

cgacgactcg gagatgagcg atggcgtgct ggagtccggg ccggttcgca tggatgtgga   2100

gcgccatgtc gtctcggtga acggtgacac catcacgctg ccgctcaagg agttcgacct   2160

gctggaatac ctgatgcgca acagcgggcg ggtgttgact cgcggacaac tgatcgaccg   2220

ggtctggggt gcggactacg tgggcgacac caagacgctc gacgtccatg tcaagcggct   2280

gcgctccaag atcgaagccg acccggctaa cccggttcac ttggtgacgg tgcgcgggct   2340

gggctacaaa ctcgagggct agcggacgcc gacaaccttg gcgactgtct ggtcggctac   2400

ggccagtgcc atcgccatga tggacagctg cgggttcact tccgggcagc tgggcaggat   2460

cgaggcgtcg gcaacccaca cgccctcgac gccgcgcagc cggcccgtcg cgtcgaccgg   2520

acaaagctgc tcgtcggcgc cggcggccgc ggtgcccgtc ggatggaagg cggccaggtg   2580

caggcttctg ggttggctc  ggcgcagcac atcctgcagc tcgggcaggg accgcatcgg   2640

tggggcgccg gggataccgg tcagcacctc caccgcgccg gcggcaaaga acagccggcc   2700

aatggcctgc agcgcgaccc gtagcttggc gatctcacct ggagctatgt catagcgcac   2760

caccgtctcg ccgcgcaccg accgcaccgt gccgacgccc cgatcggcca ccatcgcccc   2820

gaatgttgcg atctgcggcg cccggtcgag ccagcggagc agctcggccc cgtagccggg   2880

gaagaccatc gaccccatgc ccggcggtgt ggaggtggcc tcgatcagca cgccgtcgga   2940

ttcgtgaaac tcgtgaaccg ccgcgctctg cagcaccccg cgccacgcga agacgtcgtc   3000

gtcgaagagc ccggccagca tagttgccgg gtgcagcgca aggttgtggc ccagtcgcgg   3060

tgcccaccaa gaccgctgcg ccgcaacagc cctggcgtct ccgtcgcacc ggcggcgacg   3120

acgaccgcgt cggccagcac gtcgagtgtg gtgccgtcgg gccggcgggc tcgcacgcca   3180

taggcccgcc cggcgcggtg caggatcc                                      3208
```

<210> SEQ ID NO 13
<211> LENGTH: 225
<212> TYPE: DNA
<213> ORGANISM: Mycobacterium tuberculosis

<400> SEQUENCE: 13

```
gctgagccga tgacctgcgc cgacgacgat gcagagcgta gcgatgaggt gggggcacca     60

cccgcttgcg ggggagagtg gcgctgatga cctgcgccga cgacgatgca gagcgtagcg    120
```

-continued

```
atgaggtggg ggcaccaccc gcttgcgggg gagagtggcg ctgatgacct gcgccgacga    180

cgatgcagag cgtagcgatg aggaggagtg gcgctgatga ccagt                    225


<210> SEQ ID NO 14
<211> LENGTH: 25
<212> TYPE: PRT
<213> ORGANISM: Mycobacterium bovis BCG
<220> FEATURE:
<223> OTHER INFORMATION: Translation of ORF nucleotides 1525-1602 of SEQ
      ID NO:12.

<400> SEQUENCE: 14

Met Thr Cys Ala Asp Asp Asp Ala Glu Arg Ser Asp Glu Val Gly Ala
  1               5                  10                  15

Pro Pro Ala Cys Gly Gly Glu Trp Arg
             20                  25


<210> SEQ ID NO 15
<211> LENGTH: 25
<212> TYPE: PRT
<213> ORGANISM: Mycobacterium bovis BCG
<220> FEATURE:
<223> OTHER INFORMATION: Translation of ORF nucleotides 1602-1679 of SEQ
      ID NO:12.

<400> SEQUENCE: 15

Met Thr Cys Ala Asp Asp Asp Ala Glu Arg Ser Asp Glu Val Gly Ala
  1               5                  10                  15

Pro Pro Ala Cys Gly Gly Glu Trp Arg
             20                  25


<210> SEQ ID NO 16
<211> LENGTH: 25
<212> TYPE: PRT
<213> ORGANISM: Mycobacterium tuberculosis
<220> FEATURE:
<223> OTHER INFORMATION: Translation of ORF nucleotides 10-87 of SEQ ID
      NO:13.

<400> SEQUENCE: 16

Met Thr Cys Ala Asp Asp Asp Ala Glu Arg Ser Asp Glu Val Gly Ala
  1               5                  10                  15

Pro Pro Ala Cys Gly Gly Glu Trp Arg
             20                  25


<210> SEQ ID NO 17
<211> LENGTH: 25
<212> TYPE: PRT
<213> ORGANISM: Mycobacterium tuberculosis
<220> FEATURE:
<223> OTHER INFORMATION: Translation of ORF nucleotides 87-164 of SEQ ID
      NO:13.

<400> SEQUENCE: 17

Met Thr Cys Ala Asp Asp Asp Ala Glu Arg Ser Asp Glu Val Gly Ala
  1               5                  10                  15

Pro Pro Ala Cys Gly Gly Glu Trp Arg
             20                  25


<210> SEQ ID NO 18
<211> LENGTH: 17
<212> TYPE: PRT
<213> ORGANISM: Mycobacterium tuberculosis
<220> FEATURE:
<223> OTHER INFORMATION: Translation of ORF nucleotides 164-217 of SEQ
```

-continued

ID NO:13.

<400> SEQUENCE: 18

```
Met Thr Cys Ala Asp Asp Asp Ala Glu Arg Ser Asp Glu Glu Glu Trp
  1               5                  10                  15

Arg
```

<210> SEQ ID NO 19
<211> LENGTH: 39
<212> TYPE: PRT
<213> ORGANISM: Mycobacterium bovis
<220> FEATURE:
<223> OTHER INFORMATION: Translation of nucleotides 3-119 of SEQ ID NO:12, partial PgmY amino acid sequence.

<400> SEQUENCE: 19

```
Ile Pro Leu Arg Tyr Asp Leu Asp Ser Ala Met Arg Pro Leu Val Arg
  1               5                  10                  15

Gly Gly Thr Tyr Leu Asp Pro Glu Ala Ala Ala Ala Gly Ala Ala Ala
             20                  25                  30

Val Ala Gly Gln Gly Arg Gly
         35
```

<210> SEQ ID NO 20
<211> LENGTH: 410
<212> TYPE: PRT
<213> ORGANISM: Mycobacterium bovis
<220> FEATURE:
<223> OTHER INFORMATION: Translation of nucleotides 296-1528 of SEQ ID NO:12, SenX3 amino acid sequence.

<400> SEQUENCE: 20

```
Met Thr Val Phe Ser Ala Leu Leu Leu Ala Gly Val Leu Ser Ala Leu
  1               5                  10                  15

Ala Leu Ala Val Gly Gly Ala Val Gly Met Arg Leu Thr Ser Arg Val
             20                  25                  30

Val Glu Gln Arg Gln Arg Val Ala Thr Glu Trp Ser Gly Ile Thr Val
         35                  40                  45

Ser Gln Met Leu Gln Cys Ile Val Thr Leu Met Pro Leu Gly Ala Ala
     50                  55                  60

Val Val Asp Thr His Arg Asp Val Val Tyr Leu Asn Glu Arg Ala Lys
 65                  70                  75                  80

Glu Leu Gly Leu Val Arg Asp Arg Gln Leu Asp Asp Gln Ala Trp Arg
                 85                  90                  95

Ala Ala Arg Gln Ala Leu Gly Gly Glu Asp Val Glu Ser Asp Leu Ser
            100                 105                 110

Pro Arg Lys Arg Ser Ala Thr Gly Arg Ser Gly Leu Ser Val His Gly
        115                 120                 125

His Ala Arg Leu Leu Ser Glu Glu Asp Arg Arg Phe Ala Val Val Phe
    130                 135                 140

Val His Asp Gln Ser Asp Tyr Ala Arg Met Glu Ala Ala Arg Arg Asp
145                 150                 155                 160

Phe Val Ala Asn Val Ser His Glu Leu Lys Thr Pro Val Gly Ala Met
                165                 170                 175

Ala Leu Leu Ala Glu Ala Leu Leu Ala Ser Ala Asp Asp Ser Glu Thr
            180                 185                 190

Val Arg Arg Phe Ala Glu Lys Val Leu Ile Glu Ala Asn Arg Leu Gly
        195                 200                 205
```

-continued

```
Asp Met Val Ala Glu Leu Ile Glu Leu Ser Arg Leu Gln Gly Ala Glu
    210                 215                 220

Arg Leu Pro Asn Met Thr Asp Val Asp Val Asp Thr Ile Val Ser Glu
225                 230                 235                 240

Ala Ile Ser Arg His Lys Val Ala Ala Asp Asn Ala Asp Ile Glu Val
                245                 250                 255

Arg Thr Asp Ala Pro Ser Asn Leu Arg Val Leu Gly Asp Gln Thr Leu
            260                 265                 270

Leu Val Thr Ala Leu Ala Asn Leu Val Ser Asn Ala Ile Ala Tyr Ser
        275                 280                 285

Pro Arg Gly Ser Leu Val Ser Ile Ser Arg Arg Arg Arg Gly Ala Asn
    290                 295                 300

Ile Glu Ile Ala Val Thr Asp Arg Gly Ile Gly Ile Ala Pro Glu Asp
305                 310                 315                 320

Gln Glu Arg Val Phe Glu Arg Phe Phe Arg Gly Asp Lys Ala Arg Ser
                325                 330                 335

Arg Ala Thr Gly Gly Ser Gly Leu Gly Leu Ala Ile Val Lys His Val
            340                 345                 350

Ala Ala Asn His Asp Gly Thr Ile Arg Val Trp Ser Lys Pro Gly Thr
        355                 360                 365

Gly Ser Thr Phe Thr Leu Ala Leu Pro Ala Leu Ile Glu Ala Tyr His
    370                 375                 380

Asp Asp Glu Arg Pro Glu Gln Ala Arg Glu Pro Glu Leu Arg Ser Asn
385                 390                 395                 400

Arg Ser Gln Arg Glu Glu Glu Leu Ser Arg
                405                 410


<210> SEQ ID NO 21
<211> LENGTH: 227
<212> TYPE: PRT
<213> ORGANISM: Mycobacterium bovis
<220> FEATURE:
<223> OTHER INFORMATION: Translation of nucleotides 1679-2362 of SEQ ID
      NO:12, RegX3 amino acid sequence.

<400> SEQUENCE: 21

Met Thr Ser Val Leu Ile Val Glu Asp Glu Glu Ser Leu Ala Asp Pro
  1               5                  10                  15

Leu Thr Phe Leu Leu Arg Lys Glu Gly Phe Glu Ala Thr Val Val Thr
             20                  25                  30

Asp Gly Pro Ala Ala Leu Ala Glu Phe Asp Arg Ala Gly Ala Asp Ile
         35                  40                  45

Val Leu Leu Asp Leu Met Leu Pro Gly Met Ser Gly Thr Asp Val Cys
     50                  55                  60

Lys Gln Leu Arg Ala Arg Ser Ser Val Pro Val Ile Met Val Thr Ala
 65                  70                  75                  80

Arg Asp Ser Glu Ile Asp Lys Val Val Gly Leu Glu Leu Gly Ala Asp
                 85                  90                  95

Asp Tyr Val Thr Lys Pro Tyr Ser Ala Arg Glu Leu Ile Ala Arg Ile
            100                 105                 110

Arg Ala Val Leu Arg Arg Gly Gly Asp Asp Asp Ser Glu Met Ser Asp
        115                 120                 125

Gly Val Leu Glu Ser Gly Pro Val Arg Met Asp Val Glu Arg His Val
    130                 135                 140

Val Ser Val Asn Gly Asp Thr Ile Thr Leu Pro Leu Lys Glu Phe Asp
145                 150                 155                 160
```

-continued

```
Leu Leu Glu Tyr Leu Met Arg Asn Ser Gly Arg Val Leu Thr Arg Gly
            165                 170                 175

Gln Leu Ile Asp Arg Val Trp Gly Ala Asp Tyr Val Gly Asp Thr Lys
        180                 185                 190

Thr Leu Asp Val His Val Lys Arg Leu Arg Ser Lys Ile Glu Ala Asp
    195                 200                 205

Pro Ala Asn Pro Val His Leu Val Thr Val Arg Gly Leu Gly Tyr Lys
    210                 215                 220

Leu Glu Gly
225
```

FRAGMENTS OF NUCLEIC ACIDS SPECIFIC TO MYCOBACTERIA WHICH ARE MEMBERS OF THE *M. TUBERCULOSIS* COMPLEX AND THEIR APPLICATIONS FOR THE DETECTION AND THE DIFFERENTIAL DIAGNOSIS OF MEMBERS OF THE *M. TUBERCULOSIS* COMPLEX

PRIOR APPLICATION

This application is a continuation of U.S. patent application Ser. No. 09/242,588 filed May 20, 1999, now abandoned, which is a 371 of PCT/FR97/01483 filed Aug. 12, 1997.

The present invention relates to sequences of nucleic acids of mycobacteria belonging to the *M. tuberculosis* complex.

The invention likewise relates to sequences of in vitro detection of strains of mycobacteria belonging to the *M. tuberculosis* complex as well as to a method for a differential diagnosis of strains of the *M. tuberculosis* complex, especially for differentiating the presence of the BCG from that of other members of the complex in a sample.

Approximately, 1.7 billion people or ⅓ of the world population are infected with *M. tuberculosis* (Sudre et al., 1992). In 1990, the estimated number of cases of tuberculosis was 8 million, including 2.9 million deaths (Sudre et al., 1992). These last few years, the number of cases of tuberculosis in the Unites States and in Europe has increased by 3 to 6% per annum, principally in populations at high risk such as patients suffering from AIDS, chronic alcoholics, the homeless and drug addicts (Barnes et al., 1991).

Taking account of the difficulties in fighting infections by mycobacteria, there is an urgent need to be able to have a specific and sensitive rapid method allowing these infections to be diagnosed. Also, the early detection of *M. tuberculosis* in clinical samples is taking on growing importance in the control of tuberculosis both for the clinical treatment of infected patients and for the identification of exposed individuals at risk.

Detection by PCR (Polymerase Chain Reaction) of specific DNA of species of mycobacteria is probably one of the most promising novel approaches for rapid, specific and sensitive diagnosis (Saiki et al., 1985: Brisson-Noël et al., 1989; Cousins et al., 1992; Eisenach et al., 1990; Forbes et al., 1993; Fries et al., 1991; Hermans et al., 1990; Jonas et al., 1993; Kolk et al., 1992: Pierre et al., 1991; Saboor et al., 1992; Shankar et al., 1991; Sjöbring et al., 1990). The different studies carried out up to date, however, have led to different results as far as the specificity and the sensitivity are concerned. Among the reasons for this diversity, it is especially possible to note methodological differences concerning the preparation of the samples, the protocol followed for the amplification or the methods of detection of the PCR products.

Several of these studies relate to the detection by PCR of the *M. tuberculosis* complex starting from the target DNA IS6110 (Clarridge et al., 1993; Eisenach et al., 1990; Forbes et al., 1993; Noerdhoeck et al., 1994), the gene coding for the 65 kDa antigen (Brisson-Noël et al., 1991; Telenti et al., 1993), the gene coding for the 38 kDa antigen (Folgueira et al., 1993: Sjöbring et al., 1990) or the ribosomal 16S RNA (Kox et al., 1995). However, all these diagnostic tests identify the *M. tuberculosis* complex in its entirety.

The *M. tuberculosis* complex comprises *M. tuberculosis, M. bovis, M. microti* and *M. africanum*. These four species have strong homologies in their DNA (85 to 100%) (Imeada, 1985) and have several totally identical genes. This homology has limited the use of DNA sequences to differentiate the strains. It would nevertheless be of particular interest to be able to differentiate the strains of *M. tuberculosis* from those of the Calmette-Guérin (BCG) bacillus *M. bovis,* the latter often being used as live vaccines for immunoprotection against tuberculosis. Obviously, there is thus an interest in distinguishing between possibly pathogenic mycobacteria and vaccinating BCG strains. This distinction is particularly important in the case of immunodeficient individuals, such as subjects infected by HIV.

Restriction fragment length polymorphism (RFLP) analyses based on the insertion of the IS6110 elements have been used to differentiate different strains of *M. tuberculosis.* It has been shown that this insertion element allowed specific RFLP profiles of strains to be obtained on account of a variability in its localization and in the number of copies existing in the genomes of different strains. IS6110 has been demonstrated in *M. tuberculosis* and in *M. bovis* but not in the other mycobacteria tested (Cave et al., 1991). In general, several copies of this insertion element can be demonstrated in *M. tuberculosis,* although a single copy is found in *M. bovis* BCG (Cave et al., 1991). However, certain strains of *M. tuberculosis* are devoid of IS6110 (van Soolingen et al., 1994) and strains of *M. bovis* having a significant number of copies are common in some populations (van Soolingen et al., 1994). Added to these limitations is the fact that the identification of strains of *M. tuberculosis* from IS6110 necessitates Southern Blot analyses and cannot easily be carried out by routine PCR methods.

The authors of the present invention have demonstrated a novel target DNA sequence for enzymatic amplification. This sequence is part of an operon coding for a specific two-component regulatory system *M. leprae* and bacteria which are members of the *M. tuberculosis* complex. The two-component systems are regulatory systems belonging to a large family, involving two proteins which cooperate in translating external signals by modifications in the level of genetic expression (Parkinson and Kofoid, 1992). According to a proposed general model, one component localized in the membrane could act as a sensor of environmental changes and could transmit the information to a regulatory component of the response in the cytoplasm, which in turn could modulate the transcription of target genes. The communication between the two components is generally carried out by a cascade of phosphorylations.

The authors of the present invention have at present cloned and characterized a two-component mycobacterial system. This system appears to be specific to members of the *M. tuberculosis* complex and to *M. leprae.* Unexpectedly with respect to the other two-component systems, the genes of this mycobacterial system are separated by DNA sequences (intercistronic sequences or repeated sequences) which are uniquely present among the strains of mycobacteria of the *M. tuberculosis* complex and in *M. leprae.*

The authors of the present invention have additionally shown that in the strains of the *M. tuberculosis* complex, this intercistronic region corresponded to an exact or truncated number of repetitions of a sequence of 77 base pairs, SEQ ID No. 1, which was able to vary among the strains. The truncated sequence (SEQ ID No. 2) is composed of 53 base pairs and contains a short in-phase internal deletion of nucleotides Nos. 40 to 66, which are substituted by a GAG codon.

The authors of the invention have likewise shown that, surprisingly, the truncated sequence (SEQ ID No. 2) was characteristic of the members of the *M. tuberculosis* complex which are different from BCG.

In *M. leprae,* the corresponding intercistronic region is formed by a variant of 52 base pairs already additionally described and whose sequence is indicated below:

5' atg aca ccc gcg cag gcg atg atg cag agc gaa gtg acq aga ggg aat gtg a 3'(SEQ ID NO:3).

Taking account of their characteristics, these repeated sequences are of particular interest for identifying and differentiating between strains of the *M. tuberculosis* complex by enzymatic amplification techniques, such as PCR or other similar methods. More particularly, they allow a differential diagnosis between the presence of BCG and that of other members of the complex in a biological sample to be established. This differential diagnosis, whose principle is based on the specific detection of the sequence SEQ ID No. 2, forms a preferred aspect of the invention. It is advantageously employed to distinguish an infection by BCG from an infection by other virulent members of the complex in immunodefficient individuals, such as especially subjects infected by HIV.

The invention thus relates to a specific fragment of nucleic acids of mycobacteria belonging to the *M. tuberculosis* complex, comprising a sequence of nucleotides chosen from amongst the sequence SEQ ID No. 1, the sequence SEQ ID No. 2, their complementary sequences or the sequences of nucleic acids capable of hybridizing with one of the preceding sequences under conditions of high stringency.

It is likewise aimed at the use of the said sequences for the production of nucleotide probes for the in vitro detection of mycobacteria belonging to the *M. tuberculosis* complex and of oligonucleotide primers for the enzymatic amplification of specific sequences of strains which are members of the *M. tuberculosis* complex.

The invention likewise relates to a method allowing the strains of the *M. tuberculosis* complex to be differentiated from one another, particularly for allowing BCG to be differentiated from pathogenic mycobacteria of this complex.

It likewise provides means for differentiating sub-groups among the strains forming the *M. tuberculosis* complex.

In addition, it can allow *M. leprae* of the species and of the strains belonging to the *M. tuberculosis* complex to be differentiated in a biological sample.

In the context of the present invention, it is considered that the conditions of "high stringency" in which two nucleotide sequences can hybridize are the conditions defined by Sambrook et al., 1989, namely temperature conditions of between ($T_m$ minus 5° C.) and ($T_m$ minus 30° C.) and additionally preferably temperature conditions of between ($T_m$ minus 5° C.) and ($T_m$ minus 10° C.) (high stringency), $T_m$ being the melting temperature, defined as being the temperature at which 50% of the paired strands separate. Preferentially, the conditions of high stringency used correspond to prehybridization, hybridization and washing temperatures of 68° C. and a prehybridization and hybridization buffer based on 5×SSC (protocol recommended by Boehringer Mannheim).

The invention relates to a specific fragment of nucleic acids of mycobacteria of the *M. tuberculosis* complex localized in the intercistronic region of the senX3-regX3 system.

As will be explained in the examples, the sequence SEQ ID No. 1 corresponds to an entity of 77 repeated base pairs and a different number of copies according to the strains of mycobacteria studied. This repeated sequence has an open reading frame (ORF) which can code for a peptide of 25 amino acids.

The invention is thus aimed at a fragment of nucleic acids specific to the *M. tuberculosis* complex, comprising a sequence of nucleotides selected from the sequence SEQ ID No. 1, its complementary sequence or the sequence of nucleic acids capable of hybridizing with one of the preceding sequences under conditions or high stringency.

According to another aspect, the invention is aimed at a specific fragment of nucleic acids of members of the *M. tuberculosis* complex which are different from BCG, especially the virulent species *M. tuberculosis, M. africanum* or *M. bovis,* comprising a sequence of nucleotides chosen from amongst the sequence SEQ ID No. 2, its complementary sequence or the sequences of nuclear acids capable of hybridizing with one of the preceding sequences under conditions of high stringency.

As is actually illustrated by the examples, the BCG strains can be differentiated from all the other strains of the *M. tuberculosis* complex because of the absence of the sequence SEQ ID No. 1 in the senX3-regX3 intergenic region in BCG (see Table 3, groups 4, 6, 8).

The different nucleotide sequences of the invention can be of artificial origin or non-artificial origin. They can be DNA or RNA sequences.

They can be prepared, for example, by chemical synthesis, or alternatively by mixed methods including chemical or enzymatic modifications of sequences obtained by screening sequence libraries, by means of probes elaborated on the basis of the sequences SEQ ID No. 1 or 2. Such libraries can be prepared by the classical techniques of molecular biology, known to the person skilled in the art.

The nucleotide sequences of the invention allow the production of probes or of nucleotide primers capable of hybridizing specifically with these, their corresponding RNA sequences or the corresponding genes under conditions of high stringency. Such probes are likewise part of the invention. They can be used as an in vitro diagnostic tool for the detection, by hybridization experiments, of specific nucleic acid sequences of mycobacteria belonging to the *M. tuberculosis* complex.

Preferentially, the probes of the invention have at least 24 consecutive nucleotides although shorter probes can be equally suitable. At the maximum, these have the complete senX3-regX3 intergenic region of *M. tuberculosis* (IPL), namely two successive sequences SEQ ID No. 1 followed by a sequence SEQ ID No. 2. This DNA fragment contains 218 base pairs.

Among the specific preferred nucleotide probes of the members of the *M. tuberculosis* complex, the sequence SEQ ID No. 1 in its entirety or its complementary sequence appear especially.

According to another aspect, the invention is aimed at nucleotide probes for the detection and the demonstration of sequence or nucleic acids specific to members of the *M. tuberculosis* complex which are different from BCG, especially the virulent species *M. tuberculosis, M. africanum* or *M. bovis,* as well as for the differential diagnosis of the presence of BCG in a biological sample containing mycobacteria of the *M. tuberculosis* complex.

Such nucleotide probes are obtained from a region of the sequence SEQ ID No. 2 surrounding the GAG codon in position 40-42 or of its complementary strand. Preferentially, this region has a length of 21 base pairs, and contains 9 nucleotides upstream and downstream of the specific GAG codon of the sequence SEQ ID No. 2.

Advantageously, these probes comprise the sequence SEQ ID No. 2 in its entirety or its complementary sequence.

The probes of the invention hybridize according to the appropriate hybridization conditions, corresponding to the conditions of temperature and of ionic strength usually used by the person skilled in the art.

Preferentially, the probes of the invention are labelled, previously to their use. For this, several techniques are at the disposal of the person skilled in the art (fluorescent, radioactive, chemiluminiscent, enzymatic, etc. labelling).

According to a preferred embodiment, the probes are labelled with digoxygenin. Digoxygenin (DIG) is a steroid hapten coupled to dUTP for labelling DNA used as a probe. This technology is marketed by Boehringer Mannheim. After the hybridization with the probe and washing, the detection is carried out following an emission of a chemoluminescent signal by means of the substrate disodium 3-(4-methoxyspiro{1,2 dioxethane-3,2'-(5-chloro)tricyclodecan}-4-yl) phenylphosphate (CSPD).

The nucleotide sequences of the invention are likewise useful for the production and the use of oligonucleotide primers for sequencing reactions or for enzymatic amplification.

The enzymatic amplification techniques are principally illustrated by PCR. Other similar methods can, however, be used such as, for example, LCR (Ligase Chain Reaction), NASBA (Nucleic Acid Sequence Based Amplification), Q-βreplicase, SDA (Strand Displacement Amplification) and any other variant comprised in the technological knowledge of the person skilled in the art. These nucleic acid amplification techniques use oligonucleotide primer molecules to initiate the elongation reaction of the target sequence. The exact length of these primers will be able to vary according to the case. For example, as a function of the complexity of the sequence of the matrix, a polynucleotide primer typically contains from 15 to 25 nucleotides or more. In certain cases, however, it can contain less.

Preferentially, the nucleotide primers of the invention comprise at least 19 nucleotides. They are formed by primers chosen from sequences adjacent to the senX3-regX3 intergenic region, in the regions 3' of senX3 and 5' of regX3.

According to a preferred variant, the pair of primers referred to as C5 and C3 are used, namely 5'GCGCGAGAGCCCGAACTGC3' (SEQ ID NO:4) and 5'GCGCAGCAGAAACGTCAGC3' (SEQ ID NO:5) corresponding respectively to the 3' end of the senX3 gene and the 5' end of the regX3 gene. These primers respectively hybridize 56 base pairs upstream of the intercistronic region and 62 base pairs downstream of the latter.

The nucleotide sequences and the probes resulting therefrom can be cloned in cloning and/or expression vectors according to classical techniques of molecular biology, especially involving the use of restriction enzymes and of specific cleavage sites.

A preferred cloning vector in the present invention is represented by the plasmid pRegX3Mt1 deposited at the CNCM under the number I-1766 whose construction is described in greater detail in the examples below.

Another cloning vector according to the invention is represented by the plasmid pRegX3Bcl deposited at the CNCM under the number I-1765. These plasmids have each been introduced into the bacterium *E. coli* XL1-blue.

The vectors I-1765 and I-1766 have both been deposited on Aug. 7, 1996 at the CNCM (Collection Nationale de Cultures de Microorganismes, Institutes Pasteur, 25 Rue du Docteur Roux, F-75724 Paris, Cedex 15, France (under the Budapest Treaty.

The vectors I-1765 and I-1766 each contain the complete senX3-regX3 genes with the intercistronic regions of BCG and of *M. tuberculosis* respectively.

The nucleotide sequences according to the invention can additionally be expressed in appropriate systems, for the production and the study of the biological activities of the corresponding peptides. In this case, these will be placed under the control of signals allowing their expression in a cell host.

An efficient system of production of a protein or of a recombinant peptide necessitates having a vector, for example of plasmid or viral origin, and a compatible host cell.

The cell host can be chosen from prokaryotic systems, like bacteria, or eukaryotic systems, for example like yeasts, insect cells, CHO (Chinese hamster ovary) cells or any other system advantageously available.

The vector must contain a promoter, translation initiation and termination signals, as well as the appropriate regions of transcription regulation. It must be able to be maintained stably in the cell and can possibly have particular signals specifying the secretion of the translated protein.

These different control signals are chosen as a function of the cell host used. To this end, the nucleotide sequences according to the invention can be inserted into autonomic replication vectors in the chosen host, or integrative vectors of the chosen host. Such vectors will be prepared according to the methods currently used by the person skilled in the art, and the clones resulting therefrom can be introduced into an appropriate host by standard methods, such as, for example, electroporation.

The in vitro diagnostic or detection methods in which the nucleotide probes obtained from sequences of the invention are employed are likewise part of the present invention.

More particularly, the invention is aimed at a method of detection of strains of mycobacteria belonging to the *M. tuberculosis* complex in a biological sample comprising the following steps:

(i) contacting the biological sample with a pair of primers under conditions allowing hybridization of the said primers to the nucleic acids specific to strains of mycobacteria belonging to the *M. tuberculosis* complex;

(ii) amplification of the said nucleic acids;

(iii) contacting a nucleotide probe according to the invention with the said biological sample under conditions allowing the formation of hybridization complexes between the said probe and the amplified nucleic acid sequences;

(iv) detection of the hybridization complexes formed.

According to a first variant, the method according to the invention allows the presence of any member of the *M. tuberculosis* complex to be detected in a biological sample. In this case, the complexes of step (iii) defined above are formed with a specific nucleotide probe of the sequence SEQ ID No. 1 or of its complementary strand.

According to a second advantageous variant, the method of the invention allows the presence of members of the *M. tuberculosis* complex other than BCG to be specifically detected. According to this variant, the complexes of step (iii) which are detected are formed with a nucleotide probe specific to the sequence SEQ ID No. 2 or to its complementary strand, consisting preferentially of a short sequence compound of two times 9 base pairs framing the GAG codon at the specific positions 40 to 42 of the sequence SEQ ID No. 2.

According to a third particularly advantageous variant, the method of the invention allows differential diagnosis of the BCG and of other members of the complex. In this case, the method consists at first of demonstrating nucleic acids specific to all the members of the *M. tuberculosis* complex by detection according to step (iv) of the hybridization complexes formed with a first specific nucleotide probe of the sequence SEQ ID No. 1 or of its complementary strand, then in finding among the amplified nucleic acids capable of forming complexes with the said first probe those which can likewise form complexes with a second specific nucleotide probe of SEQ ID No. 2 or of its complementary strand.

The amplified nucleic acid sequences hybridizing uniquely with the first probe correspond to specific nucleic acid sequence of the BCG, although the sequences hybridizing with each of the two probes correspond to sequences of the other members of the *M. tuberculosis* complex.

This method of differential diagnosis is of obvious interest with respect to the conventional methods of detection, because it allows an infection by BCG (possibly from a vaccination) to be differentiated from that by a virulent mycobacterium of the *M. tuberculosis* complex (*M. tuberculosis, M. bovis* or *M. africanum,* and possibly *M. microti*). This distinction is particularly important in immunodeficient individuals, especially subjects infected by HIV.

According to another preferred embodiment, the invention provides a method of identification of groups of mycobacteria belonging to the *M. tuberculosis* complex, characterized in that:

the DNA of the said strains previously extracted with a pair of primers such as defined above is contacted under conditions allowing a specific hybridization of the said primers with their corresponding sequences on the DNA of the said strains and the obtainment of amplification products, and the length of the amplification products obtained is measured, for example by agarose gel electrophoresis.

Advantageously, the primers 5'GCGCGAGAGCCCGAACTGC3' (SEQ ID NO:4)and 5'GCGCAGCAGAAACGTCACC3' (SEQ ID NO:5)are used in this method.

The invention likewise relates to a kit for the in vitro identification of strains of mycobacteria belonging to the *M. tuberculosis* complex in a biological sample comprising:

a pair of primers according to the invention, as defined above;

the reagents necessary to allow the amplification of the specific sequences of nucleic acids belonging to the *M. tuberculosis* complex with the aid of the said primers, possibly means for revealing the amplified fragments, preferentially a nucleotide probe of the invention.

Other characteristics and advantages of the invention are illustrated by the example following the description as well as by the figures whose legends are indicated below.

B). Partial restriction map of the locus of the senX3 and regX3 genes of the BCG (IPP). The restriction sites are indicated with respect to the senX3 and regX3 genes, as well as the probe used.

FIG. 2: Nucleotide sequence (SEQ ID NO:12of the senX3 and regX3 genes of the BCG (IPP) and derived protein sequences: nucleotides 3 to 119 is the open reading frame (ORF) for PgmY amino acid sequence (SEQ ID NO:19); nucleotides 296 to 1528 is the ORF for the SenX3 amino acid sequence (SEQ ID NO:20); and nucleotides 1679 to 2362 is the ORF for the RegX3 amino acid sequence (SEQ ID NO:2 1). The arrows indicate palindromic sequences. The putative Shin-Dalgarno sequence is underlined in dots (SD). The predicted transmembrane sequence of SenX3 is doubly underlined. The regions of SenX3 conserved in other sensors are underlined and annotated: H, region, containing modified histidine; N, region rich in asparagine; F, region rich in phenylalanine; G1 and G2, regions rich in glycine. The small vertical arrows indicate the residues which are predicted to be phosphorylated. The annotated sequence PgmY indicates the end of the gene encoding phosphoglycerate mutase.

Figure 1A:
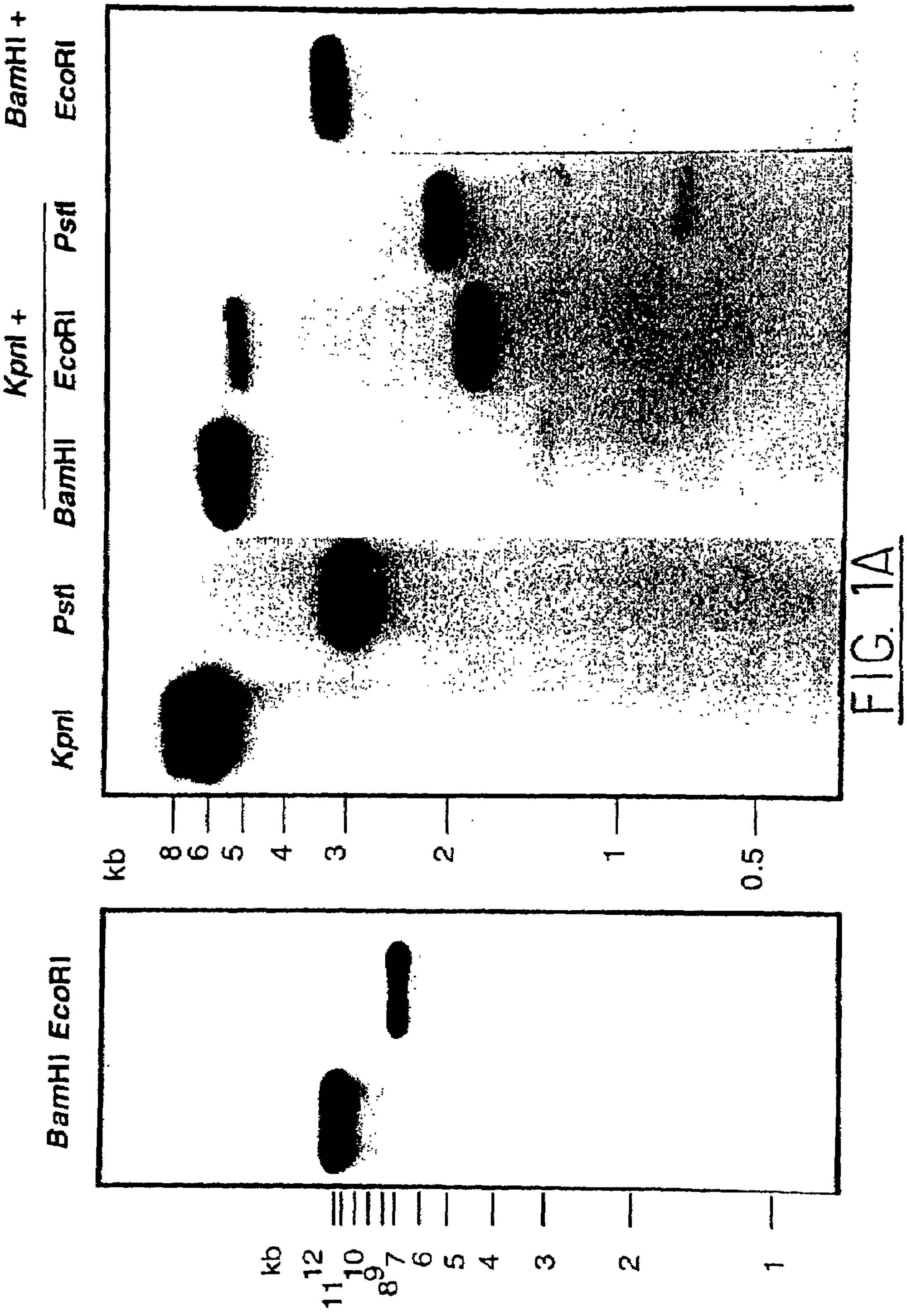
FIG. 1: "Southern Blot" analysis of the DNA of BCG (IPP). A). The fragment of 259 base pairs comprising a part of the regX3 gene was used as a probe to detect the gene in different restriction fragments in the chromosomal DNA of the BCG (IPP). The restriction enzymes used are indicated at the top of the figure.
Figure 1B:
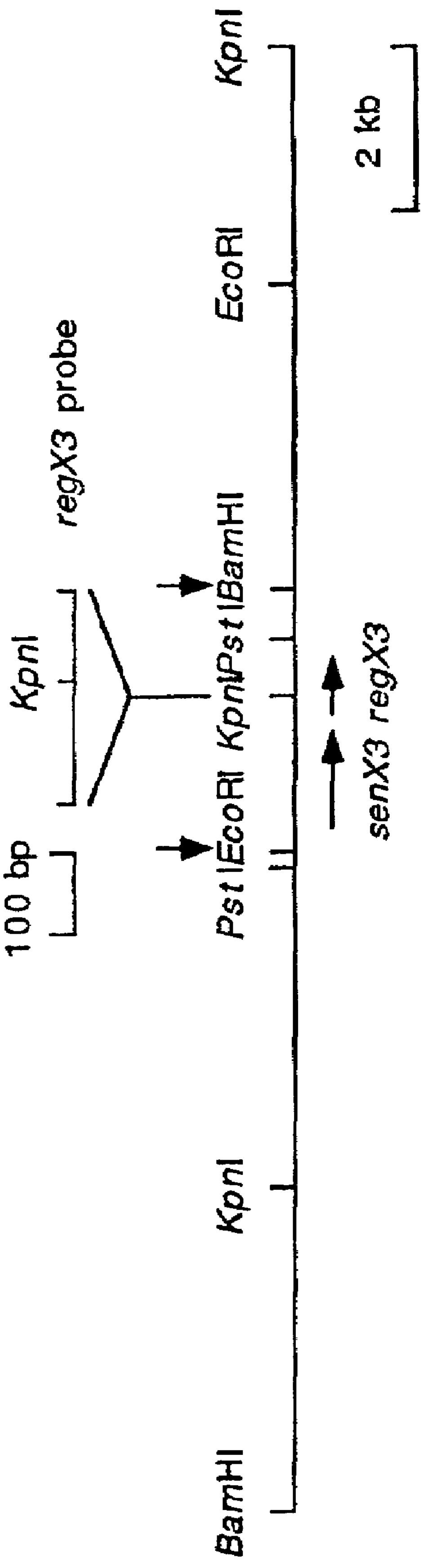
Figure 3:
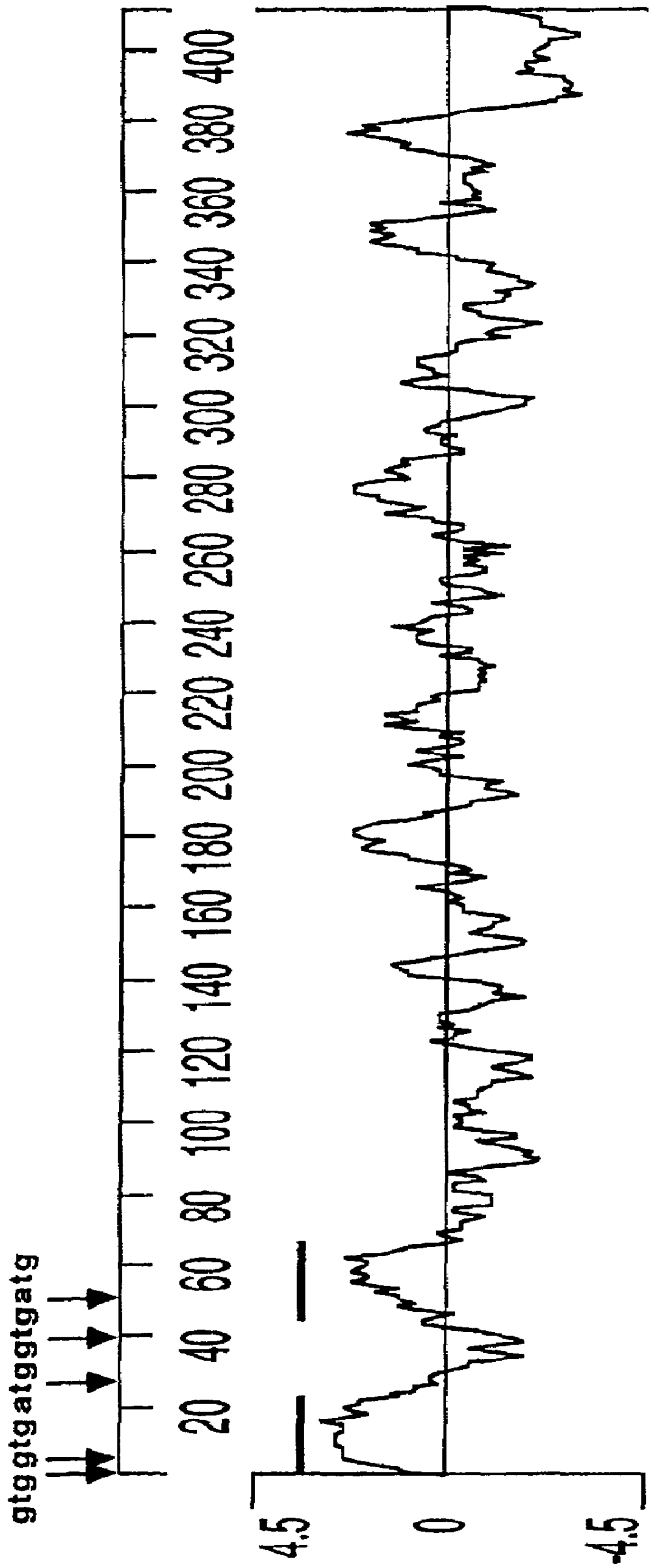

FIG. 3: hydrophobicity profile of SenX3. The positive values indicate hydrophobic regions and the negative values indicate hydrophilic regions. The arrows indicate the possible initiation codons and the two horizontal lines indicate predicted transmembrane regions. The numerals at the top of the figure indicate the numbers of amino acids.

FIG. 4: comparison of the intercistronic region_between the BCG (LPP) (nucleotides 15 16-1689 of SEQ ID NO:12) and *M. tuberculosis* (IPL) (SEQ ID NO: 13) The senX3 and regX3 genes are indicated by the arrows. The nucleotide sequences are indicated as well as the inferred protein sequences. The intercistronic region of BCG contains two open reading frames (ORFs): (1) nucleotides 1525-1602 of SEQ ID NO:12 is the ORF for SEQ ID NO:14 and (2) nucleotides 1602-1679 of SEQ ID NO:12 is the ORF for SEQ ID NO: 15. The intercistronic region of Mycobacterium tuberculosis contains three ORFs: (1) nucleotides 10-87 of SEQ ID NO: 13 is the ORF for SEQ ID NO: 16, (2) nucleotides 87-164 of SEQ ID NO: 13 is the ORF for SEQ ID NO: 17, and (3) nucleotides 164-217 of SEQ ID NO: 13 is the ORF for SEQ ID NO: 18.

Figure 5:

FIG. 5: Southern blot analysis of DNA of *M. tuberculosis* and of BCG. The chromosomal DNA of *M. tuberculosis* (IPL) (on the right) and of BCG (IPP) (on the left), was digested by PstI, subjected to electrophoresis in agarose and analyzed by hybridization with the senX3-regX3 intergenic probe of *M. tuberculosis* (IPL).

Figure 6:
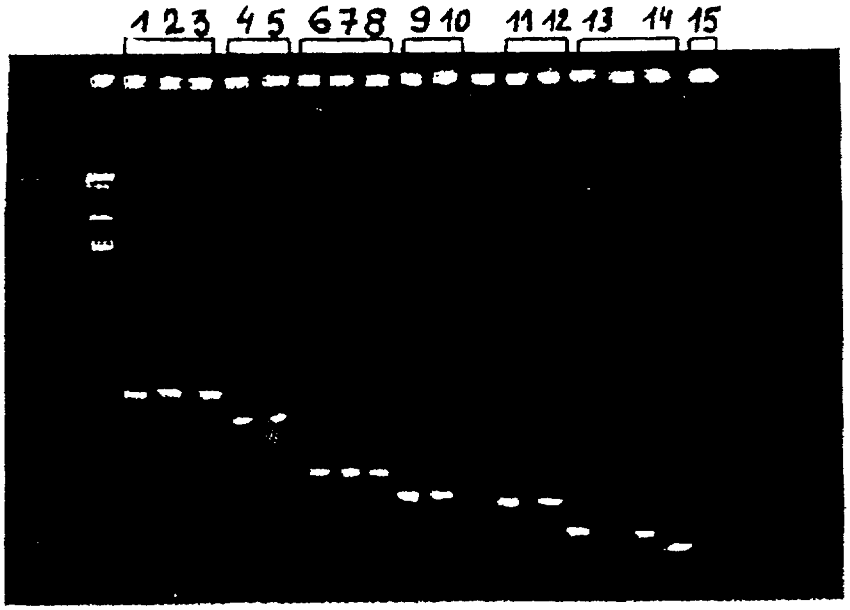

FIG. 6: analysis by electrophoresis in agarose (2.5%) of the products obtained by PCR carried out on different mycobacterial strains. Lanes 1 to 3: group 1, respectively *M. microti, M. tuberculosis* V808, *M. tuberculosis* V761; lanes 4 and 5, group 2, respectively *M. tuberculosis* V729, *M. bovis* 60; lanes 6 to 8, group 3, respectively *M. bovis* 63, *M. bovis* 78 and *M. bovis* AN5; lanes 9 and 10, group 4, respectively *M. tuberculosis* H37Ra (IPL) and *M. tuberculosis* H37Rv (IPP); lanes 11 and 12, group 5, respectively M. tuberculosis (IPL), *M. bovis* 76; lanes 13 and 14, group 6, respectively *M. bovis* (BCGite 29) and *M. bovis* BCG (IPP), lane 15, group 7, *M. tuberculosis* No. 19.

Figure 7:
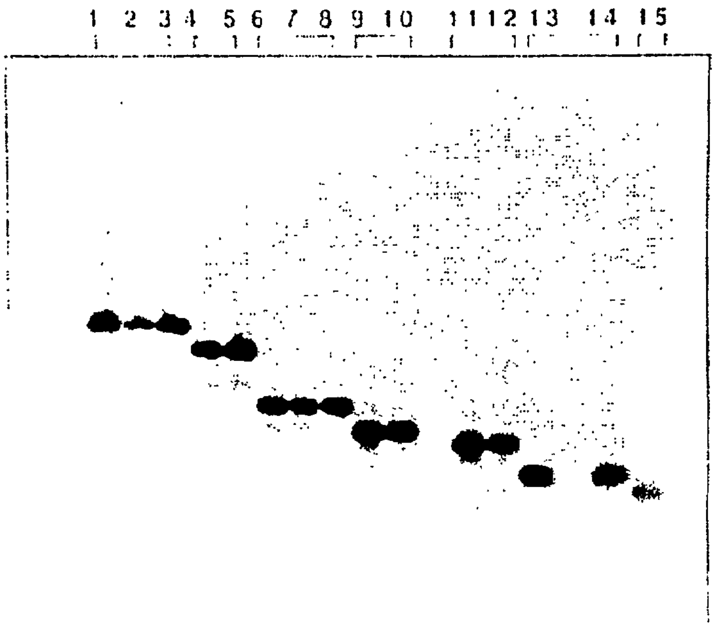

FIG. 7: Southern blot analysis of the fragments obtained in FIG. 6. The probe used is the senX3-regX3 intercistronic region of *M. tuberculosis* (IPL).

EXAMPLES

Example 1

Genomic Map and Cloning of the senX3-regX3 Genes of *M. bovis* BCG (IPP), Coding for the Two-Component Mycobacterial System Wren et al. (1992) amplified a fragment of 259 base pairs from the gene of *M. tuberculosis* (IPL) which they called regX3.

The authors of the present invention amplified the corresponding sequence from *M. bovis* BCG (vaccine strain 1173P2, obtained at the WHO collection of Stockholm, Sweden) using the following synthetic oligonucleotides: 5'-CGAGGAGTCCCTCGCCGATCCGC-3' and 5'-AGCGCCCCAGCTCCAGCCGACC-3'(SEQ ID NO:7). The amplification was carried out by using these primers and a Deep Vent polymerase (New England Biolabs). The amplification product of 259 base pairs resulting was then purified by electrophoresis on agarose gel and then sub-cloned in the Smal site of the pBluescript KS+ vector (Stratagene) according to standard protocols (Sambrook et al., 1989). This insert was then removed from the recombinant plasmid by digestion with BamHI and EcoRI and then labelled with dCTP [$\alpha$-$^{32}$P] by "random priming" (random labelling) using the "random priming" kit marketed by Boehringer according to the conditions recommended by the manufacturer. The genomic DNA of *M. bovis* BCG (IPP), cultured in Sauton medium (Sauton, 1912) at 37° C. in flasks for stationary culture of tissues, was extracted as described previously (Kremer et al., 1995a) and digested by different restriction enzymes. This DNA was then subjected to electrophoresis on agarose gel and to Southern Blot analysis according to the standard methods (Sambrook et al., 1989). The testing of the blot with the [$^{32}$P]-labelled DNA showed that digestion by KpnI with either BamHI, EcoRI or PstI produced pairs of hybridizing bands, with one band labelled more intensely than the other in each of the pairs (FIG. Ia). These bands were attributed to the 5' and 3' sequences respectively, of the unique asymmetric KpnI site of the probe. This allowed the BamHI, EcoRI and PstI 5' and 3' sites of the KpnI site to be localized (FIG. Ib). The digestions with only PstI gave a single hybridization band. As could be predicted, the digestion with KpnI gave two bands and the digestion with BamHI and EcoRI led to the obtainment of a single band of approximately 3.5 kb.

The genomic DNA of the BCG was digested with BamHI and EcoRI, and DNA fragments of 3 to 4 kb were isolated after electrophoresis on agarose gel. These fragments were inserted into pBluescript SK (Stratagene) restricted by BamHI and EcoRI. 900 recombinant clones were screened with the [$^{32}$P]-labelled probe by the said standard technique of "colony blot hybridization" (Sambrook et al., 1989). Three of them were positive and turn out to contain the same BamHI/EcoRI DNA insert of 3.2 kb by restriction analysis. A hybridizing clone was isolated for the latter studies as was named pRegX3Bcl (I-1765).

Example 2

Sequence of the Genes of *M. bovis* BCG (IPP) Coding for the Two-Component System The SalI fragments of 1.0, 1.5 and 0.7 kb were isolated from the 3.2 kb insert of pRegX3Bcl (I-1765), and sub-cloned in pBluescrip SK−. The sequence of the 3.2 kb insert, as well as that of the sub-clones SalI was determined on the two strands by the method of "primer walking". The nucleotide sequence of 3208 bp of *M. bovis* BCG (IPP) (FIG. 2) showed the frequency of C+G characteristic of the mycobacteria (66.6%). Two principal open reading frames (OFT) designated by regX3 an senX3 were identified (FIG. Ib and 2). The regX3 gene starts with an ATG triplet at the 1679 position and ends with a TAG triplet at the 2360 position. It contains the sequence of the $^{32}$P-labelled probe and codes for a protein whose inferred sequence of amino acids is 227 residues for a calculated molecular mass of 24,881 Da. The limit upstream of the senX3 ORF is not certain because five in-phase potential initiation codons (ATG or GTG) were found in a short distance (from 296 to 446) (FIGS. 2 and 3). However, only the GTG at position 296 is preceded with 9 nucleotides upstream, by sequence homologous to the Shine-Dalgarno sequence of *Escherichia coli* (4 of the 6 residues are identical to AGGAGG). Thus, this GTG codon could be the limit in 5' of the senX3 ORF which ends with the TGA strop codon at the position 1526. This ORF is thus presumed to code for a protein of 44,769 Da composed of 410 amino acid residues. The senX3 gene is preceded at 273 nucleotides upstream by the 3' part of an ORF encoding a homologue of the phosphoglycerate mutases. A sequence capable of forming a hairpin structure is localized between the positions 178 and 194. This sequence could function as a terminatory transcription sequence of the ORF upstream.

A search on the MycDB database showed that the senX3 and regX3 genes are also present in *M. leprae*. The products which they encode are respectively similar to 82.7% and 94.9% to the proteins senX3 and RegX3 of *M. bovis* (IPP). The senX3 ORF of *M. leprae* turns out to be initiated by a GTG codon and is preceded by an ORF coding for a homologue of phosphoglycerate mutase, similar to that which was found in *M. bovis* BCG (IPP).

Example 3

Cloning and Sequencing of the senX3 -regX3 Genes of *M. tuberculosis* (IPL)

The senX3 and regX3 genes of *M. tuberculosis* (IPL) were cloned by PCT from chromosomal DNA of *M. tuberculosis* 22962067, a clinical isolate from the collection of mycobacteria of the Institut Pasteur de Lille. The DNA of *M. tuberculosis* (IPL) was extracted by the method described above for the extraction of chromosomal DNA of the BCG (Kremer et al., 1995a). The fragment of 2.2 kb containing the senX3 and regX3 genes of *M. tuberculosis* (IPL) was amplified by PCR using the following primers, homologous to the adjacent sequences of the senX3 and regX3 genes of *M. bovis* BCG (IPP): 5'-TGGCGTAGTGTGTGACTTGTC-3' (SEG ID NO:8)and 5' GACCAGACAGTCGCCAAGGTT-3'(SEG ID NO:9). The amplified fragment was cloned in the SmaI site of pBluescript SK− (Version II) to produce a plasmid named pRegX3Mt1 (I-1766). The total fragment of 2.2 kb was then sequenced using the same strategy as that described in Example 2 for the senX3 and regX3 genes of the BCG (IPP). The DNA sequence of the senX3 and regX3 ORF of *M. tuberculosis* (IPL) as well as the 5' region upstream of senX3 and the 3' region downstream of regX3 were identical to those of the BCG (IPP). However, the intercistronic region between senX3 and regX3 demonstrated interesting differences which are studied in the example below.

Example 4

Analysis of the senX3-regX3 Intercistronic Region

The intercistronic region between senX3 and regX3 contains a perfect duplication of 77 base pairs in tandem in the BCG (IPP) (FIG. 4). Each repeated sequence contains a short ORF which has the capacity to code for a peptide of 25 amino acids. The ATG initiation codon which can be inferred from the first repetition overlaps the TGA stop codon of senX3. This repeated sequence ends with two stop codons in-phase, which overlap the ATG initiation codon inferred from the following repetition. The ORF of the second repetition also ends with a double TGA stop codon, which overlaps the ATG start codon of regX3.

The intercistronic region of *M. tuberculosis* (IPL) is longer and contains a third repeated sequence which, however, is not complete. It contains a short in-phase internal deletion of the nucleotides 40 to 66 which are replaced by GAG. The ORF of this third repetition also ends with a double stop codon overlapping the ATG codon of regX3.

The sequence of the intercistronic region of *M. leprae* is shorter than that of BCG (IPP). It contains 52 base pairs.

The existance of these structures in repetition in the senX3-regX3 intercistronic region led the inventors to find out whether they were present in other regions of *M. tuberculosis* (IPL) or in the chromosome of *M. bovis* BCG (IPP) by Southern Blot analysis. The senX3-regX3 intercistronic region of *M. tuberculosis* (IPL) was obtained by enzymatic digestion of pRegX3Mt2 with EcoRI and BamHI. The resulting DNA fragment of 491 base pairs was then digested with BsrI-AluI to produce a DNA fragment of 218 base pairs which corresponds to the senX3-regX3 intergenic fragment of *M. tuberculosis* (IPL). This DNA fragment was then labelled at random with digoxygenin-dUTP (kit cat. No. 10093657) according to the recommendations of the manufacturer (Boehringer Mannheim). pRegX3Mt2 was produced by a first amplification by PCR of a fragment of chromosomal DNA of 471 base pairs of *M. tuberculosis* 22962067 (IPL) using the following oligonucleotides: 5'AAACACGTCGCGGCTAATCA 3' (SEG ID NO:10) and 5'CCTCAAAGCCCCTCCTTGCGC 3' (SEG ID NO:11)and the resulting amplified fragment was then cloned in the SmaI site of pBluescript KS−.

The chromosomal DNA of *M. tuberculosis* (IPL) was then totally digested with PstI and subjected to electrophoresis on agarose gel and analysed by Southern Blot according to the customary procedures (Sambrook et al., 1989). The labelled probe was then used for hybridization as indicated below.

The probe was at first denatured by boiling for 5 minutes, and the membrane was incubated with the probe overnight at 68° C., after a prehybridization for two hours at 68° C. The buffer used for the prehybridization and the hybridization was 5×SSC (Sambrook et al., 1989), 0.1% N-laurylsarcosine (w/v); 0.2% SDS (w/v); 1% blocking reagent (Boehringer Mannheim). The membrane was then washed twice for five minutes in 2×SSC (Sambrook et al., 1989) and 0.1% SDS at ambient temperature and twice for 15 minutes in 0.1×SSC, 0.1% SDS at 68° C. The hybridized probes were then immunologically detected with antidigoxygenin Fab fragments conjugated to alkaline phosphatase and a chemiluminescent CSPD substrate (Boehringer Mannheim).

As can be seen in FIG. 5, different copies of the senX3-regX3 intercistronic region are present in *M. tuberculosis* (IPL), as well as in *M. bovis* BCG (IPP).

Example 5

Amplification by PCR of the senX3-regX3 Intercistronic Region of Different Strains of Mycobacteria Given that the intercistronic region separating the senX3 and regX3 genes has variations in length between *M. bovis* BCG (IPP), *M. tuberculosis* (IPL) and *M. leprae,* the authors of the present invention analysed the corresponding region in other strains of *M. bovis* (including non-BCG strains) and of *M. tuberculosis.* They likewise analysed other species of mycobacteria: (i) the other members of the *M. tuberculosis* complex: *M. africanum* and *M. microti* and (ii) the mycobacteria other than those of the *M. tuberculosis* complex.

The strains analysed are indicated Tables 1 and 2. Their chromosomal DNA was prepared as indicated below. The mycobacteria were recovered by centrifugation (300 revs/min; 30 minutes), starting from 100 ml of culture and incubation for 1 hour at 37° C. in 10 ml of phosphate buffer (0.4 M sucrose, 10 mM EDTA, Tris-HCl (pH 8) 10 mM, 4 mg/ml of lysozyme). The protoplasts obtained were recovered by centrifugation (3000 revs/min; 20 minutes) and then lysed by placing them to incubate for 1 hour at 60° C. in 6 ml of L buffer (10 mM NaCl, SDS 6%, 10 mM Tris-HCl (pH 8), 500 μg/ml of proteinase K). After addition of 1.5 ml of 5 M NaCl, the mixture was centrifuged (14,000 revs/min., 20 minutes). The supernatant was subjected to extraction with phenol-chloroform and the DNA was precipitated with isopropanol. The resuspended pellet was then treated with RNase, extracted with phenol-chloroform and chloroform and then precipitated with ethanol. The pellet was then dried in air and resuspended in 100 μl of TE buffer (10 mM Tris-HCl, 1 mM EDTA, pH 7.6).

The primers for PCR analysis were chosen from the DNA sequence of the senX3 and regX3 genes of *M. bovis* BCG (IPP) and *M. tuberculosis* (IPL). A primer (C5) hybridized to the 3' end of senX3 gene and had the following 5'-3' sequence: 5'GCGCGAGAGCCCGAACTGC3'(SEG ID NO:4). The other primer (C3) hybridized to the 5' end of the regX3 gene and had the following 5'-3' sequence: 5'-GCGCAGCAGAAACGTCAGC-3'(SEG ID NO:5). With these two primers, the PCR product comprises 56 additional base pairs at the 5' end of the intergenic region and 62 additional base pairs at its 3' end with respect to the intercistronic region. The PCR product has a length of 369 base pairs for *M. tuberculosis* 22962067 (IPL) and 276 base pairs for *M. bovis* BCG (IPP).

The PCR amplifications were carried out in a thermocycler (Perkin Elmer) by incubation of 1 μl of chromosomal DNA with the following reaction mixture: C5 and C3 oligonucleotides (1 μg/1 μl of each), dTNP (2 μl) 25 mM, TMACl (tetramethylammonium chloride) (2 μl) 5 mM, 10×enzymatic buffer (10 μl), Vent DNA polymerase (1 U/0.5 μl), water (82 μl). The amplification was carried out over 30 cycles at 94° C. for one minute, 65° C. for one minute and 72° C. for one minute. 10 μl of PCR product were then subjected to electrophoresis on 2.5% agarose gel and visualized with ethidium bromide. The negative controls containing all the PCR reagents except the DNA matrix were treated in parallel with the samples. The length of the PCR product was estimated by comparison with the DNA scale of 1 kb.

No PCR product was detected for the 11 strains of non-tuberculosis mycobacteria tested (see Table 2). Three strains of Streptomyces (*S. cacaoi,* S. R61 and S. R39), as well as *E. coli* TG1 likewise gave negative results in PCR. On the other hand, PCR products were obtained with all the members of the *M. tuberculosis* complex. The specificity of the PCR products was confirmed in all the cases by Southern Blot analysis using as probe the senX3-regX3 intergenic region of *M. tuberculosis* (IPL) labelled with digoxygenin, as described in Example 4.

The length of the amplified fragments is indicated in Table 3. Eight different groups with different amplicon lengths were obtained. Out of the 35 clinical isolates of *M. tuberculosis* tested, 34 gave PCR fragments of 329 base pairs which could not be distinguished from that obtained with the reference strain *M. tuberculosis* 22962067 (IPL) (group 5). One strain of *M. tuberculosis* (No. 19) gave a PCR product of 254 base pairs (Group 8). *M. tuberculosis* S200 also belongs to group 5.

Strains of *M. tuberculosis* from Vietnam and not containing the IS6110 sequence (V. 808, V. 761 and V. 729) were different from the major *M. tuberculosis* group (group 5). The length of their PCR product exceeded 500 base pairs (one product of +/−500 base pairs and two of 560). The laboratory strains of *M. tuberculosis* H37Ra and H37Rv had PCR products which were slightly larger than those obtained in group 5 of the strains of *M. tuberculosis* and these two strains are classified among group 4. These two strains are odd in as far as the uncertain pathogenicity for H37Rv and the loss of pathogenicity of H37Ra are concerned. In addition, no clinical case of *M. tuberculosis* was present in groups 4, 6, 8: these three groups are thus specific for the non-virulent strains.

The BCG strains (vaccine strains and isolates of clinical cases of BCGites) were divided into three groups (No. 4, 6 and 8). The PCR products obtained from these strains had a length of 353 base pairs, 276 and 199 respectively.

The most important variability at the level of the length of the PCR fragments was encountered for the non-BCG strains of *M. bovis*. Six strains were tested. Three of them, including the reference strains AN5, gave PCR products of 408 base pairs (group 3). The three other strains were grouped in groups 2, 5 and 7 corresponding to PCR fragments of approximately 500 and of 329 or 254 base pairs respectively.

TABLE 1

*M. tuberculosis* complex

| Species | Strains | Sources |
|---|---|---|
| *M. tuberculosis* | reference (22962067) | IPL* |
| | H37Ra | IPP** |
| | H37Rv | IPP (Marchal) |
| | S200 | CHR of Lille*** |
| | 35 clinical isolates (different profiles of IS6110 RFLP) | CHR of Lille |
| | 3 clinical isolates from Vietnam: v808, V761, V729 | IPP (Marchal) |
| *M. bovis* | BCG (vaccine strain3): | IPP |
| | BCG IPP | IPL |
| | BCG Moreau | IPL |
| | BCG Japonicu3 | IPP |
| | BCG Pragues | IPP |
| | BCG Montreal | IPP |
| | BCG Russe | IPP |
| | BCG Glaxo | |
| | case of BCGites: | |
| | 4 clinical isolates (28, 29, 30, 31) | IPL<br>CHR of Lille |
| | non BCG: | |
| | reference ANS | IPP (Marchal) |
| | 1 clinical isolates (1) | CHR of Lille |
| | 2 isolates from goats (60, 63) | University of Zaragoza (Martin) |
| | 2 isolates from cows (76, 78) | University of Zaragoza (Martin) |
| *M. africanum* | clinical isolate | |
| *M. microti* | reference ATCC 19422 | CHR of Lille<br>IPP (Marchal) |

*Institut Pasteur de Lille
**Institut Pasteur de Paris
***Centre Hospitalier Régional de Lille

TABLE 2

Atypical mycobacteria

| Species and strains | Sources |
|---|---|
| *M. aurum* | clinical isolates (IPL) |
| *M. avium* | clinical isolates (IPL) |
| *M. chelonae* | clinical isolates (IPL) |

TABLE 2-continued

Atypical mycobacteria

| Species and strains | Sources |
|---|---|
| *M. flavescens* | clinical isolates (IPL) |
| *M. fortuitum* | clinical isolates (IPL) |
| *M. kanasii* | clinical isolates (CHR of Lille) |
| *M. marinum* | clinical isolates (IPL) |
| *M. scrotulaceum* | clinical isolates (IPL) |
| *M. smegmatis* | IPL |
| *M. terae* | clinical isolates (IPL) |
| *M. xenopi* | clinical isolates (IPL) |

TABLE 3

Amplification by PCR of the senX3-regX3 intergenic region and sequencing

| | Strains of mycobacteria | Estimated length of the product obtained during PCR | Composition of the senX3-regX3 intergenic region |
|---|---|---|---|
| 1 | *M. microti*<br>*M. tuberculosis* V.808<br>V.761 | 560 bp | 77 77 77 77 77 53<br>-->-->-->-->-->-> |
| 2 | *M. tuberculosis* V.729<br>*M. bovis* 60 (goat) | ±500 bp | |
| 3 | *M. bovis* 63 (goat)<br>78 (cow)<br>AN5 | 406 bp | 77 77 77 53<br>-->-->-->-> |
| 4 | *M. tuberculosis* H37Rv (IPP)<br>*M. tuberculosis* H37Ra (IPL)<br>BCG: BCG Japonicus<br>BCGite 28<br>BCGite 30 | 353 bp | 77 77 77<br>-->-->-> |
| 5 | *M. africanum*<br>*M. bovis* 76 (cow)<br>*M. tuberculosis:*<br>reference IPL<br>S200<br>34 clinical isolates. | 329 bp | 77 77 53<br>-->-->-> |
| 6 | BCG: IPP reference<br>BCG Moreau<br>BCG Russe<br>BCG Glaxo<br>BCGite 29<br>BCGite 31 | 276 bp | 77 77<br>-->--> |
| 7 | *M. bovis* I<br>*M. tuberculosis* No. 19): one of the 35 clinical isolates of the CHR of Lille tested | 254 bp | 77 53<br>-->-> |
| 8 | BCG: BCG Pregues<br>BCG Montreal | 199 bp | 77<br>---> |

The amplified DNA fragments comprise senX3-regX3 intercistronic region as well as 56 base pairs upstream of this and 62 base pairs downstream. The arrows 77 and 53 designate the repeated elements found in each group. The strains for which the intercistronic region was sequenced are underlined.

The invention claimed is:

1. An isolated nucleic acid consisting of a nucleotide sequence selected from the group consisting of SEQ ID No: 1, SEQ ID No: 2, the complement of SEQ ID No: 1, and the complement of SEQ ID No: 2.

2. An isolated nucleic acid consisting of a nucleotide sequence selected from the group consisting of SEQ ID No: 1 and the complement of SEQ ID No: 1.

3. An isolated nucleic acid consisting of a nucleotide sequence selected from the group consisting of SEQ ID No: 2 and the complement of SEQ ID No: 2.

4. A cloning or expression vector containing a nucleic acid sequence selected from the group consisting of SEQ ID No: 1, SEQ ID No: 2, the complement of SEQ ID No: 1, and the complement of SEQ ID No: 2.

5. A vector of claim 1 which is a plasmid selected from the group consisting of pRegX3Bcl and pRegX3Mtl deposited at CNCM under Nos. I -1765 and I -1766, respectively.

6. A nucleotide probe consisting of 24 consecutive nucleotides selected from a sequence selected from the group consisting of SEQ ID No: 1, SEQ ID No: 2, the complement of SEQ ID No: 1, and the complement of SEQ ID No: 2.

7. A nucleotide probe consisting of a nucleotide sequence selected from the group consisting of SEQ ID No: 1, the complement of SEQ ID No: 1, the RNA sequence corresponding to SEQ ID NO: 1, and the RNA sequence corresponding to the complement of SEQ ID NO: 1 .

8. A nucleotide probe having a sequence comprising two successive sequences according to SEQ ID No: 1 followed by a sequence according to SEQ ID No: 2.

9. A nucleotide probe consisting of 21 consecutive nucleotides of a region of sequence SEQ ID No: 2 comprising the GAG codon in positions 40 to 42 or the complement of said 21 consecutive nucleotides.

10. A nucleotide probe consisting of nucleotides 31 to 51 of SEQ ID No: 2 or the complement thereof.

11. A nucleotide probe consisting of the sequence of SEQ ID No: 2 or the complement of SEQ ID No: 2.

12. A nucleotide probe consisting of a nucleotide sequence selected from the group consisting of SEQ ID No: 1, SEQ ID No: 2, the complement of SEQ ID No: 1, the complement of SEQ ID No: 2, the RNA sequence corresponding to SEQ ID NO: 1, the RNA sequence corresponding to the complement of SEQ ID NO: 1, the RNA sequence corresponding to SEQ ID NO: 2, and the RNA sequence corresponding to the complement of SEQ ID NO: 2, wherein said nucleotide probe is labeled by digoxygenin.

13. A nucleotide primer pair comprising a pair of primers 5'GCGCGAGACCCCGAACTGC3'(SEQ ID No: 4) and 5'GCCCAGCAGAAACGTCAGC3'(SEQ ID No: 5).

14. A method of detecting a mycobacteria strain of *M. tuberculosis* complex in a biological sample comprising the steps of:

(1) contacting the biological sample to a pair of primers 5'GCGCGAGAGCCCGAACTGC3' (SEQ ID No:

4) and 5'GCGCAGCAGAAACGTCAGC3' (SEQ ID No: 5) under conditions to effect hybridization of the primers to a nucleotide sequence of mycobacteria strains of *M. tuberculosis* complex;

(2) amplifying said nucleotide sequence with said primers;

(3) contacting said nucleotide sequences amplified from step (2) with a nucleotide probe consisting of a nucleotide sequence selected from the group consisting of SEQ ID No: 1, SEQ ID No: 2, the complement of SEQ ID No: 1, the complement of SEQ ID No: 2, the RNA sequence corresponding to SEQ ID NO: 1, the RNA sequence corresponding to the complement of SEQ ID NO: 1, the RNA sequence corresponding to SEQ ID NO: 2, the RNA sequence corresponding to the complement of SEQ ID NO: 2, nucleotides 31 to 51 of SEQ ID No: 2, and the complement of nucleotides 31 to 51 of SEQ ID No: 2 or with a nucleotide probe having a sequence comprising two successive sequences of SEQ ID No: 1 followed by a sequence of SEQ ID No: 2, under conditions for formation of hybridization complexes between said probe and said nucleotide sequences amplified from step (2); and (4) detecting the presence or absence of complexes, wherein the presence of complexes is indicative of the presence of a mycobacteria strain of *M. tuberculosis* complex.

15. The method of claim 14 wherein the nucleotide probe consists of nucleotides 31 to 51 of SEQ ID No: 2 or the complement of nucleotides 31 to 51 of SEQ ID No: 2.

16. A method of identifying groups of mycobacteria belonging to a *M. tuberculosis* complex comprising the steps of:

(1) contacting a DNA of previously extracted strains of the *M. tuberculosis* complex with a nucleotide primer pair comprising a pair of primers 5'GCGCGAGAGCCCGAACTGC3' (SEQ ID No: 4) and 5'GCGCAGCAGAAACGTCAGC3' (SEQ ID No: 5) to obtain amplification products; and (2) measuring a length of the amplification products obtained from step (1), wherein said length of the amplification products enables determining the group to which said strains of *M. tuberculosis* complex belong.

17. A kit for in vitro identification of strains of mycobacteria of a *M. tuberculosis* complex in a biological sample comprising a pair of primers 5'GCGCGAGAGCCCGAACTGC3' (SEQ ID No: 4) and 5'GCGCAGCAGAAACGTCAGC3' (SEQ ID No: 5).

18. A method of detection and of differential diagnosis of BCG and the members of *M. tuberculosis* complex in a biological sample comprising the steps of:

(1) contacting the biological sample to a nucleotide primer pair comprising a pair of primers 5'GCGCGAGAGCCCGAACTGC3' (SEQ ID No: 4) and 5'GCGCAGCAGAAACGTCAGC3' (SEQ ID No: 5) under conditions to effect hybridization of the primers to nucleotide sequences of mycobacteria of *M. tuberculosis* complex;

(2) amplifying said nucleotide sequences with said primers;

(3) contacting the biological sample containing said nucleotide sequences amplified from step (2) with a nucleotide probe having a sequence comprising two successive sequences SEQ ID No: 1 followed by a sequence SEQ ID No: 2 under condition for formation of hybridization complexes between said probe and said nucleotide sequences amplified from step 2;

(4) detecting any first hybridization complexes present; and (5) determining if said first hybridization complexes are also capable of forming second hybridization complexes with a nucleotide probe, the sequence of which consists of nucleotides 31 to 51 of SEQ ID No: 2, or the complement of nucleotides 31 to 51 of SEQ ID No: 2, for detection of sequences of nucleic acids of *M. tuberculosis* complex other than BCG, the presence of said second hybridization complexes being indicative of the presence of a *M. tuberculosis* strain different from BCG and the presence of said first hybridization complexes uniquely being indicative of BCG.

19. The method of claim 18, wherein the biological sample is from an immunodeficient human.

20. The method of claim 19, wherein the human is infected with HTV.

* * * * *